United States Patent [19]

Longman et al.

[11] Patent Number: 5,232,666
[45] Date of Patent: Aug. 3, 1993

[54] CAM-DRIVEN FLOW SYSTEM FOR USE WITH ANALYTICAL INSTRUMENTS

[75] Inventors: Millard Longman, Tamarac; Oscar Proni, Hollywood, both of Fla.

[73] Assignee: Abbott Laboratories, Abbott Park, Ill.

[21] Appl. No.: 760,719

[22] Filed: Sep. 16, 1991

Related U.S. Application Data

[63] Continuation-in-part of Ser. No. 347,521, May 4, 1989, abandoned.

[51] Int. Cl.⁵ ............................................. G01N 33/00
[52] U.S. Cl. ............................................ 422/67; 422/63; 422/81; 436/43; 73/864.23; 141/130
[58] Field of Search ............... 422/63, 67, 81; 436/43; 73/864.23; 141/130

[56] References Cited

U.S. PATENT DOCUMENTS

| | | |
|---|---|---|
| 3,800,984 | 4/1974 | Phelan . |
| 3,948,605 | 4/1967 | Atwood et al. ........................ 422/63 |
| 3,948,607 | 4/1976 | Atwood et al. ........................ 422/63 |
| 4,447,395 | 5/1984 | Englar et al. ........................ 422/63 X |
| 4,889,613 | 12/1989 | McNeal et al. ................... 422/63 X |
| 5,094,818 | 3/1992 | Longman et al. ................. 422/81 X |

*Primary Examiner*—Robert J. Warden
*Assistant Examiner*—Stephanie Blythe
*Attorney, Agent, or Firm*—Richard D. Schmidt

[57] ABSTRACT

Liquid transport system with constant fluid flow rate provided by cam driven pump. Multiple cams on common cam shaft are driven by a source of constant power and coordinate timing and operation of multiple system elements.

7 Claims, 2 Drawing Sheets

CAM-DRIVEN FLOW SYSTEM FOR USE WITH ANALYTICAL INSTRUMENTS

This is a continuation-in-part application of U.S. Ser. No. 07/347,521 filed on May 4, 1989, now abandoned.

BACKGROUND OF THE INVENTION

This invention relates to an apparatus and method for effecting liquid transport in the liquid flow systems commonly used in analytical instruments. More particularly the invention relates to liquid flow systems requiring an essentially constant flow rate therein. Additionally, the invention relates to a coordinated cam-driven scheme to effect the timing and operation of multiple system elements while providing the means for effecting an essentially constant rate of liquid flow within a liquid conduit.

Early liquid handling devices used in analyzers such as the Coulter Counter ® particle analyzers, used a simple vacuum pump, connected to a vacuum bottle to smooth pressure variations, and a series of manually operated stop cock controls to effect the movement of fluids in the instrument. This system is cheap, reliable and of limited use in modern automated instruments.

In the more simple of the analytical devices, a plurality of cams can be positioned on a single shaft and operate upon a single function of the device. In U.S. Pat. No. 4,631,483 to Oscar Proni et al. the power supply is provided in the form of a weight attached to a bellows. The operator lifts the weight and then releases it so that the free fall of the weight expands the bellows and thereby creates a vacuum in the liquid transport system. The purpose for this approach lays in the fact that Proni's system requires a constant or nearly constant pressure on the bellows to produce the liquid flow. The present invention is directed to a system which requires a constant flow rate. Such an analyzer is described in U.S. Pat. No. 5,094,818 to Longman, et al. and is hereby incorporated by reference.

In current automated counters a large capacity pump or pumps are used to generate both pressure and vacuum. The liquid flow is controlled with pinch valves. The timing of the pinch valve operation is accomplished electronically or by a series of cams which operate to turn on and off electrical contacts which in turn operate motors or drivers. The electric drivers can be used to effect operation of the pinch valves. Where multiple mechanical or system functions are integrated within a single device, or where the mechanical or system functions are difficult to synchronize, separate drive systems, operating at separate speeds upon separate mechanical or system functions, is generally required. The net effect of such perceived difficulties has been to design the various subassemblies of an instrument with separate power supplies or drive systems and the integration or synchronization of their various functions with a microprocessor and elaborate software programs. This leads to increased costs, complexity and generation of internal heat.

As mentioned earlier cam activated piston systems are known. However, in systems requiring a constant flow cams and cam followers are not used to effect such a result. For example in an internal combustion engine cams and cam followers are used to time when the valves open and close. The cam scheme in the engine does not operate to control the rate at which these events occur. Other than the obvious rate of once every cycle the cams do not effect the rate at which the valves open and close. The fuel supply system of the internal combustion engine, which requires and controls a constant flow rate within it, is not controlled or effected by the cam system. The fuel system uses an entirely separate system. The same is true in the prior art analyzers. Pistons, cams and cam followers are used for timing but not for creating or controlling a constant flow rate.

U.S. Pat. No. 4,631,483 discussed above recognized that a cam system could be used to replace the function of an operator, that of raising the weight, but to enable the weight to operate properly the cam could not be followed by a cam follower on the release of the weight or down stroke.

It is an object of the present invention to provide a reliable, inexpensively manufactured fluid transport system having an essentially constant flow rate therein.

It is a further object of this invention to eliminate the need for multiple electronic drivers or electronic timing controls in a constant flow rate liquid flow system.

SUMMARY OF THE INVENTION

The above and other objects are attained in accordance with the present invention by providing a liquid transport system for use in an analytical instrument where the liquid transport system is driven by a power source providing constant rotational power to a power shaft. The power source is responsive to signals from a means capable of detecting the rotational position of the power shaft. Cams corresponding to at least one piston pump means in fluid communication with a fluid conduit and at least one valve means are located along the power shaft and the cams are mechanically coupled to their corresponding functional element. Additionally, the cams corresponding to the piston pump means are configured so as to enable the pump means to create a liquid flow rate within the liquid conduit that is essentially constant. Additional elements of the analytical instrument whether or not directly associated with the liquid transport system may also be mechanically coupled to the power shaft and cams.

Preferably, the coupling means is a cam follower and spring attached to the pump means or valve means to insure constant contact with the corresponding cam and the rotational detection means comprises a sensor for detecting any of a predetermined number of rotational positions from an optically encoded element which is disposed on the shaft or a cam. The rotational detection means will then generate and transmit a signal to enable the power means to begin, stop or reverse the supply of power to the power shaft.

BRIEF DESCRIPTION OF THE DRAWINGS

In the following description of a preferred embodiment of the invention, reference is had to the accompanying drawings, in which.

DETAILED DESCRIPTION OF THE PREFERRED EMBODIMENT

Figure 1:
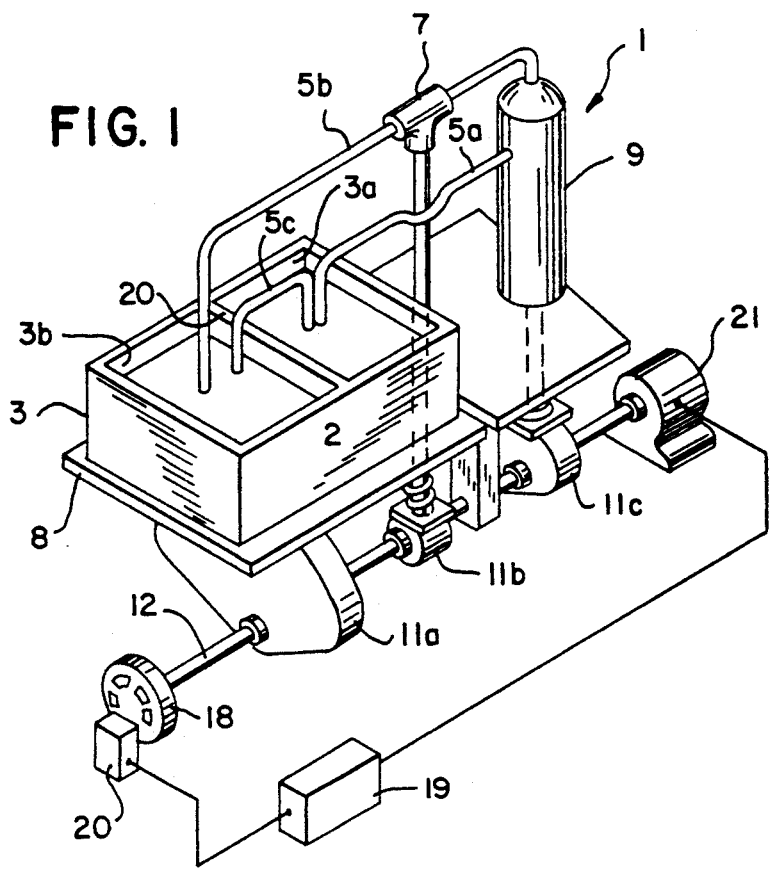
FIG. 1 is a plan view of the liquid transport system of the present invention.

In FIG. 1, the liquid transport system is generally referred to by numeral 1 and includes a sample liquid 2 housed in container 3. Container 3 is divided by wall 20 into two reservoirs 3a and 3b. The liquid sample 2 resides in reservoir 3a while a reagent 4 is housed in reservoir 3b. In a common example, the liquid is a diluted blood sample to be analyzed for red and white blood cell counts and the reagent is an isotonic solution of salt water.

Figure 2A:
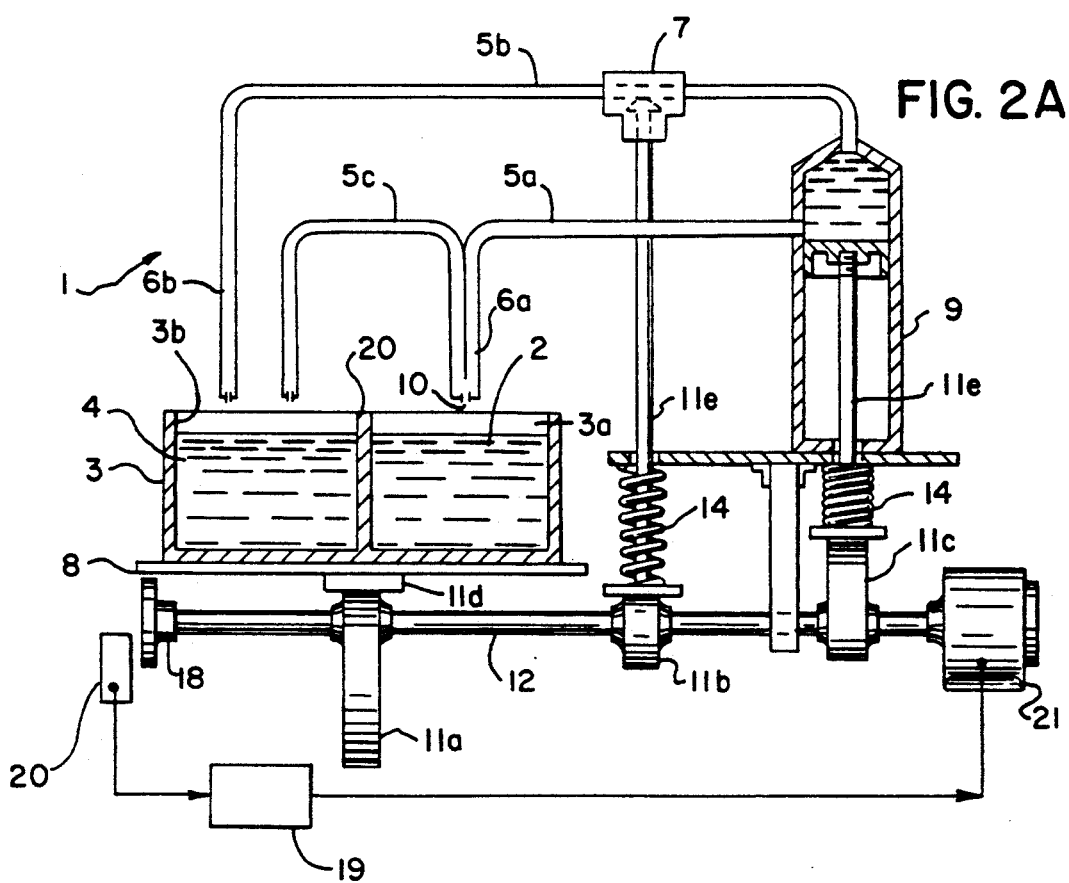
FIGS. 2A–2C are front elevational views at various stages of operation of the system of FIG. 1.
Figure 2B:
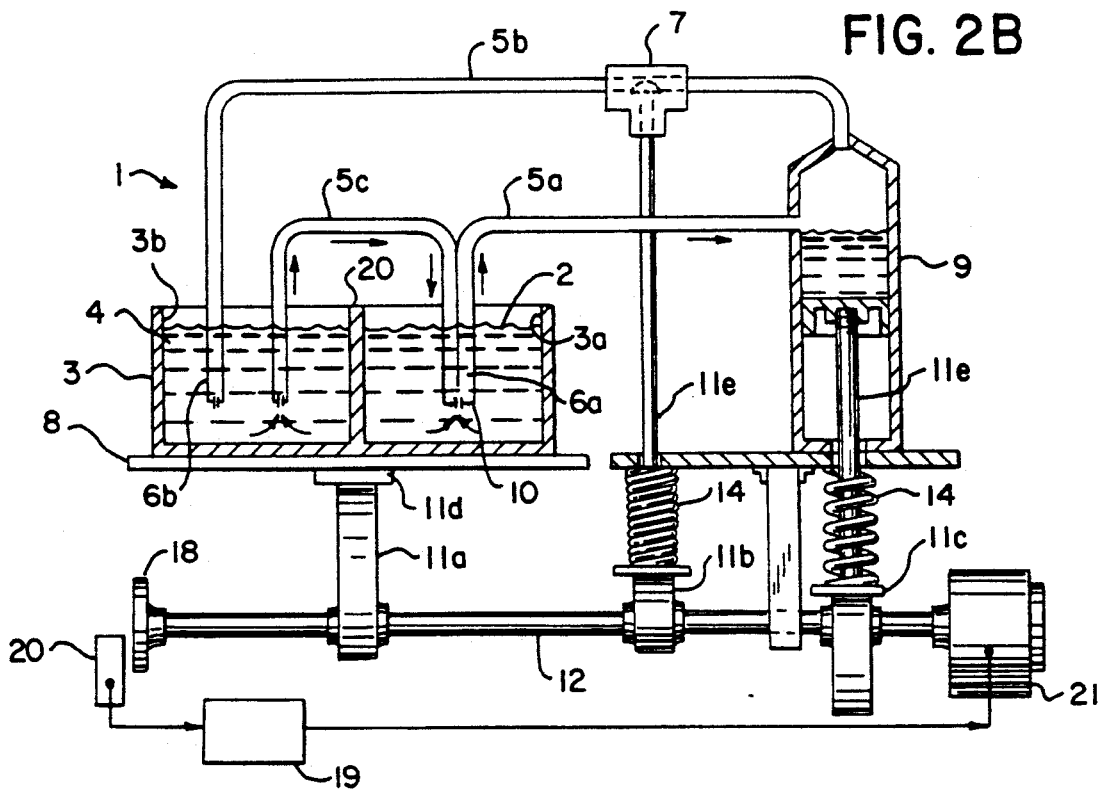

Referring also to FIGS. 2A and 2B, a first liquid path is defined by a tube 5a having open end 6a for immersion in the liquid 2 and a second end in contact with pump 9. Open end 6a is provided with a conventional metering aperture 10. The metering aperture 10 typically has a sensor (not shown) associated with it for counting the amount of analyte passing by it. Also not shown are the associated counting electronics. A second liquid path is defined by a tube 5b having a first apertured end 6b immersed in the reagent 4 and a second end also in contact with pump 9. A pinch valve 7 is disposed along the second liquid path to restrict liquid flow from the reservoir 3b to the pump 9. A third liquid path is defined by interconnecting tube 5c which allows liquid contact between reservoirs 3a and 3b to a point just behind the metered aperture 10 and as, described in U.S. Pat. No. 5,094,818 to Longman et al. and hereby incorporated by reference.

In the simple example shown in FIG. 1, three functional system elements are shown for the purpose of illustration. Again, those of ordinary skill in the art will realize that the system of the present invention could be expanded to include any number or types of devices, such as bellows pumps, other platforms and other system controls, for performing any number of system functions.

A series of cams 11a, 11b and 11c are disposed along a common cam shaft 12 relative to the position of platform 8, pinch valve 7 and piston pump 9. The platform 8, pinch valve 7 and piston pump 9 are mechanically coupled to the cam 11a, 11b and 11c by cam followers 11d, 11e and 11f. The cam followers translate the rotational movement of the cams to translational movement in order to cause the mechanically coupled system element to perform its intended function. Activation and maintenance of the performance of each system element is coordinated by the relative shape of each cam to the other. It is easily understood that one or more elements may need to be activated during the operative cycle of one or more of the other system elements in order to synchronize the instrument cycle.

The cam followers 11d, 11e and 11f may be integrated with the bottoms of platform 8, pinch valve 7 and piston pump 9, respectively, or they may be separate elements attached in an appropriate manner. The contact force required to hold cam followers 11d, 11e and 11f in intimate contact with the cams 11a, 11b and 11c, respectively, is supplied by appropriate means such as springs 14. The method of contact is not critical, the only requirement for the cam follower-system element connection is that the cam follower engage with a portion of the system element which can be mechanically manipulated to cause the element to perform its intended function.

Cams 11a, 11b and 11c are designed such that the contact of the cam followers, as they follow circumferential path of the rotating cams, causes the corresponding system element to perform its intended function at the necessary time in the liquid transport cycle. In addition, the configuration of the cams associated with a pump is such that the stroke of the piston in the cylinder creates an essentially constant liquid flow rate in the liquid path or conduit with which it is in fluid communication. For purposes of this invention essentially constant means that the fluid flow rate does not vary sufficiently to adversely affect the detection means of the analytical instrument in which the liquid transport system of this invention is installed. In the preferred particle counting analyzer herein described the variation in flow rate is preferably no greater than $+/-$ one percent. A preferred configuration for the cam is known in the art as a Archimedes Spiral. In such a configuration the radius taken from the center of the cam to the cut in the cam surface decreases linerally with angular rotation. In other words, for every degree of rotation the radius always decreases by the same amount.

Figure 2C:
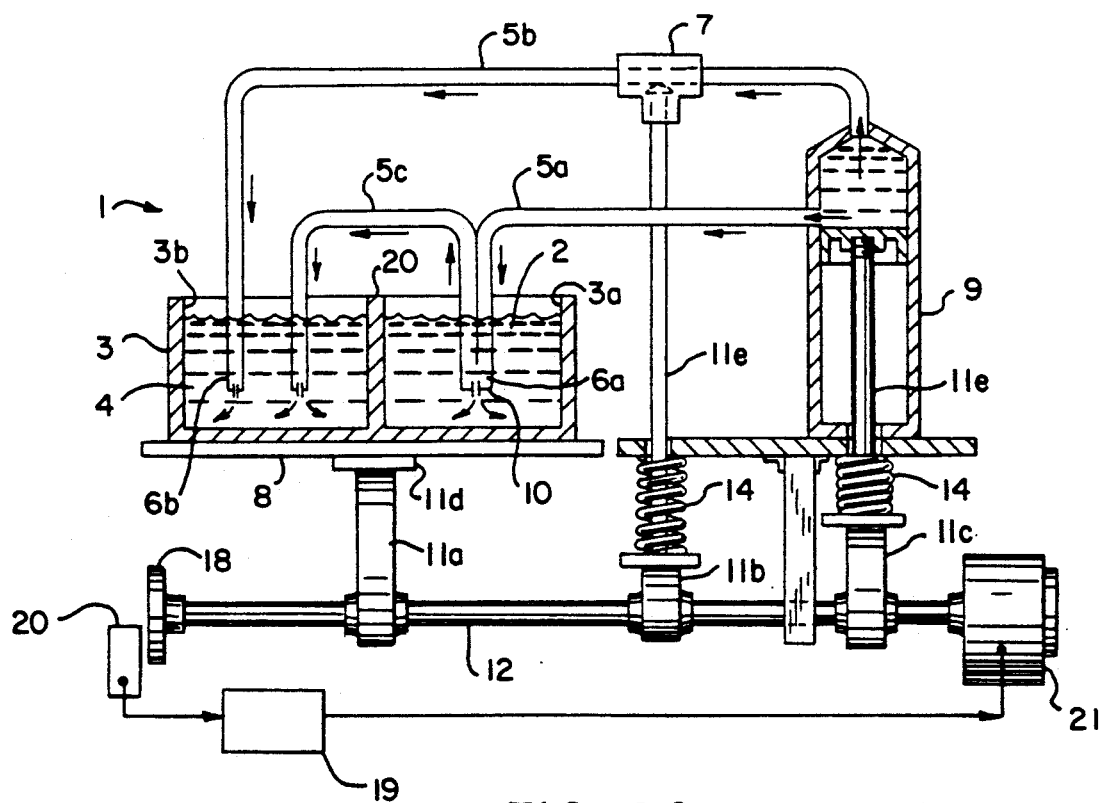

In a typical cycle, cam 11a will first raise platform 8 to immerse the apertured ends of the tubes in the liquids, as shown in FIG. 2B. The cam 11b closes valve 7 and then activates pump 9 to draw a predetermined amount of liquid 2 from the reservoir 3a through aperture 10 into tube 5a, while preventing liquid from being drawn into tube 5b from reservoir 3b. Typically, the liquid flow is reversed as in FIG. 2C, after a satisfactory amount of liquid has been drawn, in order to pump the sampled liquid back into the reservoirs 3a and 3b, which may thereafter be discarded along with their contents. Cam 11c is designed such that pinch valve 7 is opened before cam 11b causes pump 9 to reverse the liquid flow. Cam 11a can then lower platform 8 to complete the cycle as shown in FIG. 2A. The system may also be designed to route the liquid drawn from the container 3 through a series of pinch valves to a waste container (not shown).

In order to stop, start and reverse the direction of the motor 21 there is provided a controller 19. The motor 21 turns at a constant speed of one shaft revolution per instrument cycle. Preferably, the controller 19 is configured such that it cannot change the speed of the motor 21 during an instrument cycle. It is to be understood that the speed of the motor may be varied between cycles or before operation.

The control of motor 21 and thus the coordination of the instrument cycle is effected by controller 19 with input from an optical encoder 18 and corresponding sensing means 20. The rotational position of the shaft, as indicated by the relative position of the optically encoded element 18, is detected by the optical sensor and interpreted by the controller 19 as an associated stage in the instrument cycle. Predetermined controller outputs are sent to motor 21 based on the rotational position information obtained from the optical encoder 18. The number of shaft positions indicated by the optical encoder 18 is a matter of design, based on the configuration and application of the system 1.

The preferred embodiment having been set forth herein, it is to be understood that there can be deviation and modification without departing from the true scope and essence of the disclosed invention.

We claim:

1. In a cam driven liquid transport system of the type for use with an analytical instrument having a liquid sample receiving means and a liquid transport system for selectively drawing liquid from the sample receiving means and into the liquid transport system for transporting the liquid therefrom, the liquid transport system including a pump having a pump chamber with an inlet port and an outlet port, a pump piston in the chamber and adapted for expanding and contracting the chamber, a first transfer conduit having one end coupled to the inlet port and an opposite, inlet end positioned for drawing liquid from the sample receiving means, a second transfer conduit having one end coupled to the outlet port and an opposite end adapted for discharging the liquid, and a valve system in line with the second conduit and selectively movable between variable opened and closed positions, an improvement comprising:

a rotatably driven power shaft;

a plurality of eccentric cams mounted along the power shaft;

a cam follower operatively coupled to each cam, a first of said cam and cam follower combinations in communication with the liquid sample receiving means for selectively placing the liquid sample receiving means in and out of communication with the inlet end of the first transfer conduit, and a second of said cam and cam follower combinations in communication with said pump for driving the piston and selectively expanding and contracting the pump chamber; and a sensor in association with the power shaft for indicating the rotational position thereof, such that the liquid sample receiving means, the pump and the valve system cooperate to produce a constant liquid flow rate in the liquid transport system.

2. The liquid transport system of claim 1, further including a power supply for driving the power shaft, wherein the power supply is adapted for responding to said sensor for controlling the rotational position of the power shaft.

3. The liquid transport system of claim 1, including means for operating the valve system in a corresponding relationship to the rotational position of the power shaft.

4. The liquid transport system of claim 3, wherein said means for operating the valve system comprises a third cam and cam follower combination, said third cam and cam follower combination in communication with the valve system for selectively varying the position of the valve system in the second conduit in response to rotational position of the power shaft.

5. The liquid transport system of claim 1, including a detector placed in the inlet end of the first conduit. amend the remaining claims, as follows:

6. The liquid transport system of claim 1 wherein there is further included means for effecting constant contact between said cam follower and said corresponding cam.

7. The liquid transport system of claim 1 wherein said sensor comprises an optically encoded element disposed on said power shaft for indicating a plurality of predetermined number of rotational positions of said power shaft and a sensing element for reading and detecting said optically encoded element for signaling the detected position of said shaft.

* * * * *